United States Patent
Olli

Patent Number: 6,008,410
Date of Patent: Dec. 28, 1999

[54] KETIMINE

[75] Inventor: Larry K. Olli, Seattle, Wash.

[73] Assignee: The Boeing Company, Seattle, Wash.

[21] Appl. No.: 08/992,601

[22] Filed: Dec. 17, 1997

[51] Int. Cl.$^6$ .................................................. C07C 273/00
[52] U.S. Cl. ................. 564/57; 564/59; 528/49; 528/53; 528/54; 528/59; 528/60; 528/62; 528/64; 528/65
[58] Field of Search ......................... 564/57, 59; 528/49, 528/53, 54, 59, 60, 62, 64, 65

[56] References Cited

U.S. PATENT DOCUMENTS

| | | | |
|---|---|---|---|
| 3,789,045 | 1/1974 | Coury et al. | 260/18 |
| 4,009,307 | 2/1977 | Erikson et al. | 427/377 |
| 5,739,194 | 4/1998 | Natesh et al. | 524/457 |

FOREIGN PATENT DOCUMENTS 26 30 013   12/1978   Germany .

OTHER PUBLICATIONS

Wicks, et al., "The Direct Reaction Between Ketimines and Aliphatic Isocyanates," Water–Borne & Higher Solids and Powder Coatings Symp. Feb., 1993.

Hill, et al., "High Solids Coatings Based on a Novel Tri-isocyanate," Waterborne, Higher Solids and Powder Coatings Symp., Feb. 1995 pp. 200–210.

*Primary Examiner*—Peter O'Sullivan
*Attorney, Agent, or Firm*—John C. Hammar

[57] ABSTRACT

Aliphatic tetraketimine of the present invention are a novel class of compounds represented by the formula:

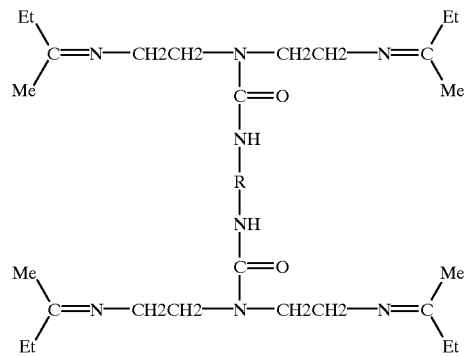

wherein Et is ethyl, Me is methyl, and R is a residue of an aliphatic diisocyanate. The tetraketimine is made by condensing a novel ketimine with a diisocyanate. The ketimine has a free secondary amine after a polyamine selected from the group consisting of:

H2N—C2H4—NH—C2H4—NH2,
H2N—C2H4—NH—C2H4—NH—C2H4—NH2,
H2N—(CH2)6—NH—(CH2)6—NH2, or
tris(2-aminoethyl)amine is reacted with a ketone.

9 Claims, No Drawings

KETIMINE

TECHNICAL FIELD

The present invention relates to an aliphatic or alicyclic ketimine and to its corresponding polyamine which are usable in coatings, composites, or adhesives.

BACKGROUND OF THE INVENTION

Polyamines has found widescale application in the preparation of composites, such as nylons and other polyamides or heterocycles such as imides, oxazoles, or thiazoles. The usefulness of the polyamines, however, is sometimes impacted by their reactivity. To slow and to control their reaction, we have discoverd that the amine functionalities can be blocked with ketones to form novel ketimines. The ketimines might be used as latent moisture cure resins in epoxy coatings or in two-part polyurethane systems where the ketimine evolves to the polyamine and reacts with an isocyanate or reacts directly with the isocyanate, as described in Dr. D. Wicks et al., "The Direct Reaction Between Ketimines and Aliphatic Isocyanates," Water-Borne & Higher-Solids and Powder Coatings Symposium, Feb. 24–26, 1993, which we incorporate by reference.

SUMMARY OF THE INVENTION

The ketimine of the present invention is one component of a novel class of tetraketimines or polyamines useful as latent moisture cure resins or components in composites. The preferred tetraketimine is typically aliphatic and of reasonably high molecular weight to provide toughness with relatively high crosslinking but without brittleness. The tetraketimine is generally made by condensing a diisocyanate with a triamine having two, blocked primary amines and one free secondary amine. A preferred tetraketimine has the formula:

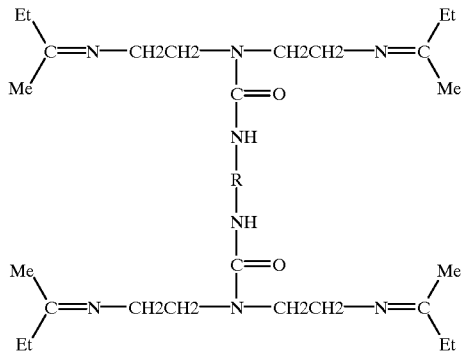

wherein Et is ethyl, Me is methyl, and R is a residue of a diisocyanate, and, preferably, an aliphatic or alicyclic hydrocarbon.

DETAILED DESCRIPTION OF A PREFERRED EMBODIMENT

The preferred tetraketimine of the present invention has four, protected amine functional groups that evolve into a four-functional primary amine to react with a corresponding isocyanate or that react directly with the isocyanate to form a urethane. If moisture causes the ketimine evolve into a polyamine, the ketimine releases a ketone, such as acetone, MEK, MiBK, or an alicyclic ketone (such as cyclopentanone or cyclohexanone), which is a common solvent with a relatively low vapor pressure. The preferred ketimine has aliphatic character and appreciable molecular weight.

A preferred polymer made with the ketimine of the present invention includes residues of the tetraketimine and a polyisocyanate mixed in generally stoichiometric proportions with a small amount of solvent. The tetraketimine is made by condensing a diisocyanate with a polyamine, and generally a triamine having two, blocked primary amines and one secondary amine. The polyamine is generally selected from the group consisting of

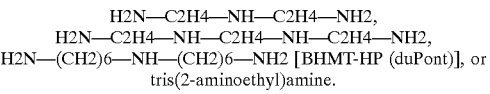

Prior to its mixing with the isocyanate, the primary amines of the polyamine are blocked with a ketone to form a ketimine. Then the secondary amine of the ketimine condenses with the isocyanate to yield the tetraketimme.

The polyisocyanate is preferably a diisocyanate, and can be any readily commercially available isocyanate, such as triaminononane triisocyanate (TAN, which is most commonly 4-aminomethyl-1,8-diaminooctane), hexamethylenediisocyanate (HDI), HDI-Trimers, such as Desmodur N-3300® from Miles, Luxate HT2000® from Olin, or Tolonate HDT® from Rhone-Poulenc, 2-Heptyl-3,4-bis(9-isocyanatononyl)-1-pentylcyclohexane and other C12 to C36 aliphatic and alicyclic diisocyanates, meta-tetramethylxylyenediisocyanate, hydrogenated methylenebisphenylene diisocyanate, isophorone diisocyanate (IPDI-Trimer), and the like.

A corresponding polymer can be made by the condensation of the diisocyanate directly with the polyamine. We prefer to proceed through the tetraketimine, however, because we can control the polymerization reaction better through stepwise reactions.

Pigments (including flatting agents or dispersants) might be added to the polymer and are described in the CRC Handbook of Chemistry & Physics, which we incorporate by reference. These pigments comprise 1–40 wt % or, perhaps, 1–50 wt % of the coating, and typically from 40–50 wt %. The particular application will dictate the ratio of pigment to binder and the concentrations of the various pigment constituents.

While I have described a preferred embodiment, those skilled in the art will understand modifications, alterations, or additions that can be made to the preferred embodiment without departing from the present invention. Therefore, interpret the application liberally to protect the invention in terms of its preferred embodiment and its full range of equivalents. Interpret the claims broadly restricting their scope only as necessary in view of the pertinent prior art.

I claim:

1. A polyurea, aliphatic tetraketimine, comprising:

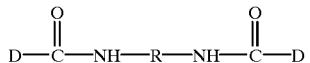

wherein R is a residue of 2-Heptyl-3,4-bis(9-isocyanatononyl)-1-pentylcyclohexane; and D is a residue of a diketimine made by reacting

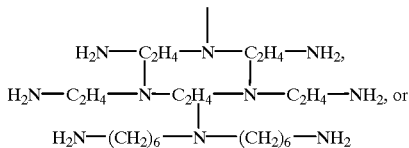

with a ketone selected from acetone, methyl ethyl ketone, MiBk, or a lower alicyclic ketone.

2. A method for making a polymer, comprising the steps of:

reacting the ketimine of claim 1 with a polyisocyanate coreactant.

3. The method of claim 2 wherein the coreactant is a diisocyanate.

4. The method of claim 3 wherein the diisocyanate is aliphatic or alicyclic without any hydrocarbon unsaturation.

5. The method of claim 2 wherein the coreactant is an aliphatic diisocyanate.

6. The method of claim 5 wherein the diisocyanate is 2-Heptyl-3,4-bis(9-isocyanatononyl)-1-pentylcyclohexane.

7. An aliphatic, polyurea tetraketimine, having the formula:

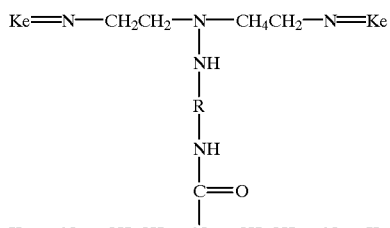

wherein Ke is a residue of a ketone, and R is a residue of 2-Heptyl-3,4-bis(9-isocyanatononyl)-1-pentylcyclohexane.

8. The tetraketimine of claim 7 wherein the ketone is acetone, methyl ethyl ketone, MiBK, or a lower alicyclic ketone.

9. A method for making a polyurea, aliphatic tetraketimine, comprising the step of reacting

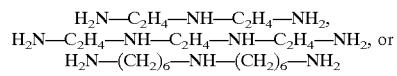

with a ketone and 2-Heptyl-3,4-bis(9-isocyanatononyl)-1-pentylcyclohexane.

* * * * *

UNITED STATES PATENT AND TRADEMARK OFFICE
CERTIFICATE OF CORRECTION

PATENT NO.   : 6,008,410                                         Page 1 of 1
DATED        : December 28, 1999
INVENTOR(S)  : Larry K. Olli It is certified that error appears in the above-identified patent and that said Letters Patent is hereby corrected as shown below:

Column 3, claim 1,
Lines 2-7, please insert a line space after each line of text in the formula in order to create three separate compounds $$-- H_2N-C_2H_4-\overset{|}{N}-C_2H_4-NH_2,$$

$$H_2N-C_2H_4-\overset{|}{N}-C_2H_4-\overset{|}{N}-C_2H_4-NH_2, \text{ or}$$

$$H_2N-(CH_2)_6-\overset{|}{N}-(CH_2)_6-NH_2 \quad --$$

Signed and Sealed this

Fourth Day of December, 2001

Attest:

NICHOLAS P. GODICI
*Attesting Officer*    *Acting Director of the United States Patent and Trademark Office*